United States Patent
Sato et al.

(10) Patent No.: US 10,845,448 B2
(45) Date of Patent: Nov. 24, 2020

(54) MAGNETIC RESONANCE IMAGING DEVICE AND IMAGING METHOD USING SAME

(71) Applicant: Hitachi, Ltd., Tokyo (JP)

(72) Inventors: Yoshitaka Sato, Tokyo (JP); Katsunari Nagashima, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/342,005

(22) PCT Filed: Dec. 1, 2017

(86) PCT No.: PCT/JP2017/043347
§ 371 (c)(1),
(2) Date: Apr. 15, 2019

(87) PCT Pub. No.: WO2018/110329
PCT Pub. Date: Jun. 21, 2018

(65) Prior Publication Data
US 2019/0250234 A1    Aug. 15, 2019

(30) Foreign Application Priority Data
Dec. 15, 2016   (JP) ................................ 2016-243474

(51) Int. Cl.
*G01R 33/565* (2006.01)
*A61B 5/00* (2006.01)
(Continued)

(52) U.S. Cl.
CPC ........ *G01R 33/5659* (2013.01); *A61B 5/0037* (2013.01); *A61B 5/055* (2013.01);
(Continued)

(58) Field of Classification Search
USPC ........................................................ 324/309
See application file for complete search history.

(56) References Cited

U.S. PATENT DOCUMENTS 7,821,264 B2    10/2010  Koch
2013/0187651 A1*  7/2013  Konta ............. G01R 33/56383
                                                324/309
(Continued)

OTHER PUBLICATIONS

International Search Report with English translation and Written Opinion issued in corresponding application No. PCT/JP2017/043347 dated Feb. 27, 2018.
(Continued)

*Primary Examiner* — Rodney E Fuller
(74) *Attorney, Agent, or Firm* — Foley & Lardner LLP (57) ABSTRACT

A magnetic resonance imaging device includes a control unit configured to set a plurality of frequency bands within a predetermined frequency range. A subject is caused to be irradiated with a high-frequency magnetic field pulse having one of the frequency bands from a transmission unit. A reception unit is caused to receive a nuclear magnetic resonance (NMR) signal generated by the subject. An image generation unit is caused to generate an image from the NMR signal while changing the frequency band. A plurality of images corresponding to the plurality of frequency bands are obtained, and a composite of the plurality of images is obtained. The frequency bands are set so that adjacent frequency bands partially overlap each other. A bandwidth of the frequency bands is narrowest for the frequency band including a specific frequency within the frequency range, and widens in a direction away from the specific frequency.

10 Claims, 6 Drawing Sheets

(51) Int. Cl.
 *A61B 5/055* (2006.01)
 *G01R 33/54* (2006.01)
(52) U.S. Cl.
 CPC ...... *G01R 33/543* (2013.01); *G01R 33/56563* (2013.01); *G01R 33/56572* (2013.01)

(56) References Cited

U.S. PATENT DOCUMENTS

2016/0154080 A1   6/2016  Wiens
2017/0059674 A1*  3/2017  Koh .................. G01R 33/3664

OTHER PUBLICATIONS

International Preliminary Report on Patentability issued in corresponding International Application No. PCT/JP2017/043347, dated Jun. 27, 2019.

* cited by examiner

FIG. 7 ered to as "MRI") device, and
MAGNETIC RESONANCE IMAGING DEVICE AND IMAGING METHOD USING SAME

TECHNICAL FIELD

The present invention relates to a magnetic resonance imaging (hereinafter, referred to as "MRI") device, and particularly to a technique for reducing image distortion due to a metal embedded in a subject.

BACKGROUND ART

The MRI device is a device which measures NMR signals generated by atomic nuclear spins constituting tissues of a subject, particularly a human body, and two-dimensionally or three-dimensionally images the form and function of the head, abdomen, extremity, and the like of the human body. When measuring the NMR signal at the time of photographing, the NMR signal is given a phase encoding amount and is frequency-encoded by a gradient magnetic field, and the NMR signal is measured as time series data. The measured NMR signal is reconfigured into an image by being subjected to two-dimensional or three-dimensional Fourier transformation.

In recent years, there has been an increasing demand for performing MRI imaging on a subject embedded in a body with an implant corresponding to a conditional MRI. When metal is contained in the implant, a magnetic field is generated as the metal is magnetized by a static magnetic field $B_0$ generated by the MRI device, and distortion occurs in the static magnetic field $B_0$ and the gradient magnetic field around the metal. For that reason, in an obtained image, strong distortion occurs around the metal in a frequency direction and a slice direction.

In order to reduce this distortion, in PTL 1, a high frequency magnetic field of one frequency band is repeatedly irradiated while reducing the distortion in the slice direction by not applying a gradient magnetic field for selecting the slice position to receive a plurality of the NMR signals to generate a three-dimensional image. This operation is performed in each of a plurality of frequency bands having different center frequencies to obtain a plurality of three-dimensional images with different irradiated high frequency bands. By compositing the obtained three-dimensional images, a composite three-dimensional image is obtained. With this configuration, in the technique of PTL 1, distortion due to metal in the slice direction and the frequency direction is reduced.

CITATION LIST

Patent Literature

[PTL 1] U.S. Pat. No. 7,821,264

SUMMARY OF INVENTION

Technical Problem

However, in an imaging method of PTL 1, since it is necessary to perform an operation of irradiating a high frequency magnetic field of one frequency band a plurality of times to acquire a plurality of NMR signals and to generate a three-dimensional image for each of a plurality of frequency bands, a long imaging time is required. By reducing the number of the frequency bands, the imaging time is shortened, but the effect of reducing the image distortion due to the metal also decreases. For that reason, the imaging time and the distortion reduction effect are in a trade-off relationship.

An object of the present invention is to provide an MRI device capable of shortening imaging time while reducing distortion of an image caused by disturbance of a magnetic field by metal in a subject.

Solution to Problem

In order to achieve the object described above, according to the present invention, there is provided a magnetic resonance imaging device including a static magnetic field generation unit that generates a uniform static magnetic field in a space for accommodating a subject, a transmission unit that irradiates a high-frequency magnetic field pulse for exciting the subject, a reception unit that receives an NMR signal generated by the subject irradiated with the high-frequency magnetic field pulse, an image generation unit that generates an image from the NMR signal, and a control unit. The control unit sets a plurality of frequency bands within a predetermined frequency range, causes the subject to be irradiated with the high-frequency magnetic field pulse having one of the plurality of frequency bands from the transmission unit, causes the reception unit to receive the NMR signal generated by the subject, causes the image generation unit to repeatedly perform an operation for generating the image from the NMR signal while changing the frequency bands, obtains a plurality of images respectively corresponding to the plurality of frequency bands, and composites the plurality of images. In this case, the control unit sets the plurality of frequency bands so that adjacent frequency bands partially overlap each other. A bandwidth of the plurality of frequency bands is narrowest for the frequency band including a specific frequency within the frequency range, and stepwisely or continuously widens in a direction away from the specific frequency.

Advantageous Effects of Invention

According to the present invention, it is possible to shorten the imaging time while reducing the image distortion caused by the disturbance of the magnetic field due to the metal within the subject.

BRIEF DESCRIPTION OF DRAWINGS

FIG. 6 (a) is a graph illustrating bins (frequency bands) of the high-frequency magnetic field pulse of a pre-scan in the embodiment and the maximum intensity A(i) of the NMR signal obtained by the pre-scan of the bins.

DESCRIPTION OF EMBODIMENTS

Hereinafter, embodiments of the present invention will be described in detail with reference to the drawings. In all drawings, those having the same function are given the same reference numerals, and repetitive description thereof will be omitted.

<<Overall Configuration of MRI Device>>

Figure 1:
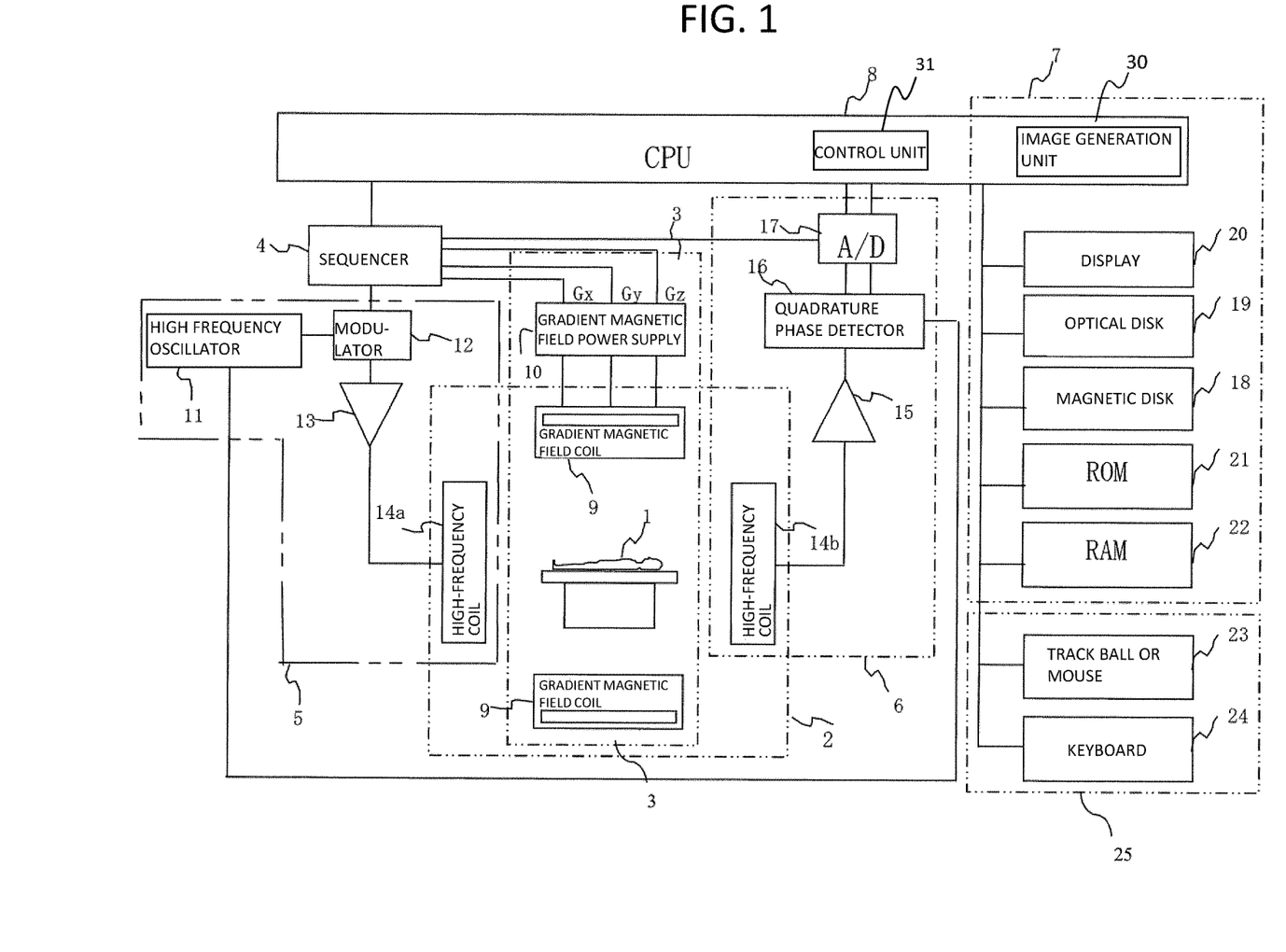
FIG. 1 is a block diagram for explaining the overall configuration of an MRI device according to an embodiment of the present invention.

First, an outline of an overall configuration of an example of an MRI device according to the present invention will be described with reference to FIG. 1. FIG. 1 is a block diagram illustrating the overall configuration of the MRI device of the embodiment. The MRI device obtains a tomographic image of a subject using an NMR phenomenon, and as illustrated in FIG. 1, is configured to include a static magnetic field generation system 2, a gradient magnetic field generation system 3, a transmission system 5, a reception system 6, a signal processing system 7, a sequencer 4, and a central processing unit (CPU) 8.

In a case of a vertical magnetic field method, the static magnetic field generation system 2 generates a uniform static magnetic field in a direction orthogonal to a body axis of a subject 1 in a space around a subject 1, and in a case of a horizontal magnetic field method, the static magnetic field generation system 2 generates a uniform static magnetic field in a body axis direction. In order to generate the uniform magnetic field, the static magnetic field generation system 2 includes a static magnetic field generating source of a permanent magnet type, a normal conducting type or a superconducting type.

The gradient magnetic field generation system 3 includes a gradient magnetic field coil 9 for applying a gradient magnetic field in three axial directions of X, Y and Z which are the coordinate system (stationary coordinate system) of the MRI device and a gradient magnetic field power supply 10 for driving each gradient magnetic field coil, and applies gradient magnetic fields Gx, Gy, and Gz in the three axial directions of X, Y, and Z by driving the gradient magnetic field power supply 10 of each coil in accordance with an instruction from the sequencer 4 to be described later.

The sequencer 4 performs control to repeatedly apply a high-frequency magnetic field pulse (hereinafter, referred to as "RF pulse") and a gradient magnetic field pulse to the subject 1 in a predetermined pulse sequence. The sequencer 4 operates under the control of the CPU 8 and sends various instructions necessary for collecting tomographic images of the subject 1 to the transmission system 5, the gradient magnetic field generation system 3, and the reception system 6, thereby performing control to execute a pulse sequence.

The transmission system 5 irradiates a high-frequency magnetic field pulse (hereinafter, also referred to as an RF pulse) of the subject 1 in order to cause nuclear magnetic resonance at nuclear spins of atoms constituting the living tissue of the subject 1. The transmission system 5 includes a high frequency oscillator 11, a modulator 12, a high frequency amplifier 13, and a high frequency coil (transmission coil) 14a on a transmission side. The high frequency oscillator 11 generates an RF pulse signal at the timing according to a command from the sequencer 4. The RF pulse signal is amplitude-modulated by the modulator 12, and the amplitude-modulated RF pulse signal is amplified by the high frequency amplifier 13, and then supplied to the high frequency coil 14a disposed close to the subject 1, thereby irradiating the subject 1 with the RF pulse.

The reception system 6 detects an echo signal (NMR signal) emitted by nuclear magnetic resonance (NMR) of atomic nuclear spins constituting the living tissue of the subject 1, and includes a high frequency coil (reception coil) 14b on the reception side, a signal amplifier 15, an quadrature phase detector 16, and an A/D converter 17. The NMR signal emitted from the subject 1 excited by the RF pulse irradiated from the high frequency coil 14a on the transmission side is detected by the high frequency coil 14b disposed close to the subject 1, amplified by the signal amplifier 15, divided into signals of two systems orthogonal to each other by a quadrature phase detector 16 and detected at the timing according to an instruction from the sequencer 4, and each of the signals is converted into a digital quantity by the A/D converter 17 and sent to the signal processing system 7.

In FIG. 1, the high frequency coil 14a of the transmission system 5 and the gradient magnetic field coil 9 are installed so as to face the subject 1 in the case of the vertical magnetic field system and to surround the subject 1 in the case of the horizontal magnetic field system, in the static magnetic field space of the static magnetic field generation system 2 into which the subject 1 is inserted. In addition, the high frequency coil 14b on the reception side is installed so as to face or surround the subject 1.

The CPU 8 functions as a control unit 31 that controls the sequencer 4 to execute imaging by reading and executing a program stored in advance in the ROM 21 by the CPU 8 and an image generation unit 30 that generates an image of the subject 1 from the NMR signal detected by the reception system 6. In this embodiment, the control unit 31 and the image generation unit 30 are configured to realize their functions by software, but some or all of their functions can be realized by hardware such as an application specific integrated circuit (ASIC) or a field-programmable gate array (FPGA).

The image generation unit 30 constitutes a signal processing system 7 together with a storage device such as an optical disk 19, a magnetic disk 18, a ROM 21, a RAM 22, a display 20 composed of a CRT or the like. The signal processing system 7 performs various data processing and display and storage of processing results. When data from the reception system 6 is input to the CPU 8, the CPU 8 functions as the image generation unit 30 for executing processing such as signal processing and image reconfiguration. The image generation unit 30 displays the generated image on the display 20 and records the image on the magnetic disk 18 or the like of the external storage device.

An operation unit 25 inputs various types of control information of the MRI device and control information of processing to be performed by the signal processing system 7, and is configured to include a track ball or mouse 23, a keyboard 24, and the like. The operation unit 25 is disposed close to the display 20, and the user interactively controls various processing of the MRI device through the operation unit 25 while watching the display 20.

At present, a nuclide to be imaged of the MRI device is a hydrogen nucleus (proton) which is a main constituent substance of the subject, as a clinically widely used substance. By imaging information on spatial distribution of proton density and spatial distribution of the relaxation time of an excited state, an image of the form or function of the human head, abdomen, limbs and the like is captured in two or three dimensions.

<<Operation of Control Unit 31 and Image Generation Unit 30>>

The operation of the control unit 31 and the image generation unit 30 of the MRI device of the present embodiment will be described. In the MRI device of the present embodiment, in order to shorten the imaging time while reducing distortion due to metal within the subject, the control unit 31 controls each unit to image the subject 1 as follows.

Figure 2:
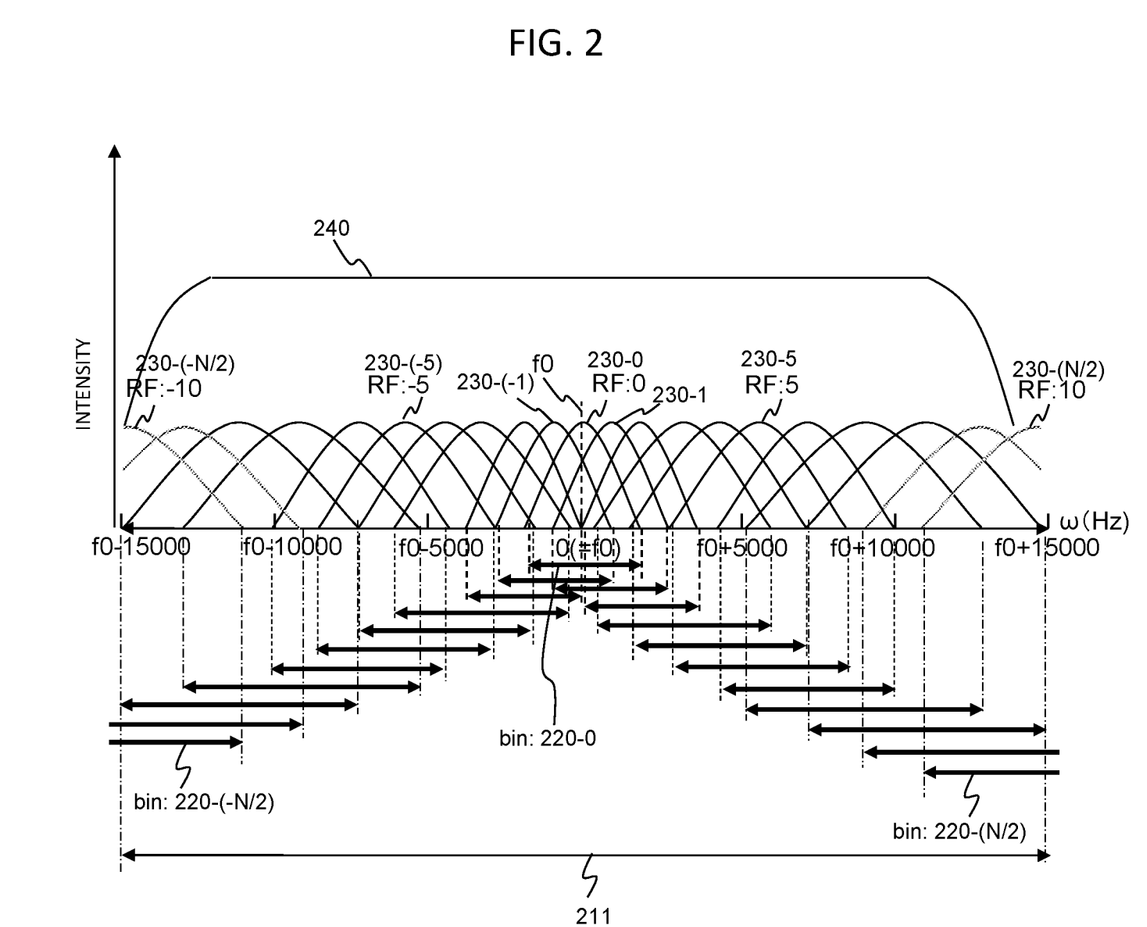
FIG. 2 is an explanatory diagram illustrating a profile of a high-frequency magnetic field pulse at the time of imaging and its frequency band in the embodiment.

FIG. 2 is an explanatory diagram illustrating a frequency band set by the control unit 31 and an intensity profile of the high-frequency magnetic field pulse in the frequency direction. As illustrated in FIG. 2, the control unit 31 sets a plurality of frequency bands (N+1 bands) (hereinafter, also referred to as bins) 220-(−N/2) to 220-0 to 220-(+N/2) in a predetermined frequency range 211, and transmits a high-frequency magnetic field pulse 230-0 having one frequency band (for example, 220-0) among the plurality of frequency bands to the subject 1 from the transmission unit (transmission system 5). The NMR signal generated by the subject 1 is received by the reception unit (reception system 6). With this configuration, the control unit 31 acquires the number of NMR signals necessary for imaging, and causes the image generation unit 30 to generate an image from the NMR signal received by the reception system 6.

The control unit 31 repeatedly performs the operation described above while changing the plurality of frequency bands (N+1 frequency bands) 220-(−N/2) to 220-(+N/2), and obtains N+1 three-dimensional images that respectively correspond to N+1 frequency bands 220-(−N/2) to 220-(+N/2), and composites N+1 images, thereby obtaining a composite image.

In this case, the control unit 31 sets such that adjacent frequency bands of the frequency bands 220-(−N/2) to 220-(+N/2) partially overlap. The control unit 31 sets each of the frequency bands 220-(−N/2) to 220-(+N/2) so that the bandwidth of the frequency band including a specific frequency f0 (220-0 in the example of FIG. 2) is the narrowest and the bandwidth widens stepwise or continuously in a direction away from the specific frequency f0.

As described above, by setting the frequency bandwidth narrower around the specific frequency f0 and setting the frequency bandwidth wider stepwisely or continuously in a direction away from the specific frequency f0, the number of frequency bands (N) can be reduced. Further, it is possible to obtain the composite image reflecting the NMR signal having a frequency far from a specific frequency f0 while reflecting the NMR signal having frequencies around the specific frequency f0 in the image with a high contribution ratio. Accordingly, while the NMR signal having the frequency around the specific frequency f0 is reflected to the image with a high contribution ratio to improve accuracy of the entire image, a metal peripheral region in which the excitation frequency of the NMR signal is shifted due to the disturbance of the magnetic field by the presence of the metal is excited with a high-frequency magnetic field pulse in a frequency band far from the specific frequency f0 to make it possible to acquire the NMR signal and reflect the NMR signal to the image. Therefore, the number of frequency bands can be reduced as compared with the conventional imaging method, the imaging time can be shortened, and a highly accurate image reflecting the NMR signal in the metal peripheral region can be obtained.

It is preferable to select the frequency fp at which intensity of the NMR signal becomes maximum as the specific frequency f0 in consideration of the matters that the peak position coincides with intensity distribution of the NMR signal when the metal is not implanted and the intensity distribution becomes broad, in frequency distribution of the intensity of the NMR signal of the subject in which the metal is implanted in the body.

Further, the control unit 31 may execute pre-scanning in order to obtain frequency distribution of NMR signal intensity of the subject 1. For example, the control unit 31 causes the subject 1 to be irradiated with a high-frequency magnetic field pulse of a plurality of preset frequencies constituting the predetermined frequency range from the transmitter (transmission system 5), and causes the reception unit (reception system 6) to receive an NMR signal generated by the subject 1 for each of a plurality of frequencies. The control unit 31 may set the frequency fp of the high-frequency magnetic field pulse at which the NMR signal of the maximum intensity is obtained to the specific frequency f0.

The control unit 31 may cause the bandwidth of the frequency band to be set to correspond to the intensity of the NMR signal obtained in the frequency band by pre-scan. For example, the bandwidth is set to be wider in accordance with the NMR signal intensity as the frequency band is more apart from the specific frequency f0 and the intensity of the NMR signal is smaller.

It is desirable to set the high-frequency magnetic field pulses 220-(−N/2) to 220-(+N/2) so as to have intensity distribution within the frequency band. It is preferable that a profile 240 obtained by summing the intensities of the overlapping high-frequency magnetic field pulses 220-(−(N−1)/2) to 220-(+(N−1)/2) is continuous in the frequency direction, as illustrated in FIG. 2, in the intensity distribution.

The control unit 31 may be configured to set a plurality of frequency bands by selecting one type from among a plurality of types of frequency band patterns prepared in advance. The plurality of types of frequency band patterns are patterns designed in advance such that at least one of the bandwidths of the frequency bands 220-(−(N−1)/2) to 220-(+(N−1)/2) and a degree of overlapping of adjacent frequency bands is different.

An operation unit 25 that receives information on the metal embedded in the subject 1 from the operator may be further included. In this case, the control unit 31 may select one type from the plurality of types of frequency band patterns according to the metal information received by the operation unit 25 from the operator.

Further, the control unit 31 may execute the pre-scan described above and may select a pattern of frequency bands from plurality of types of frequency band patterns based on the obtained intensity distribution of NMR signals. It is desirable to prepare a storing unit that stores patterns of a plurality of types of frequency bands. For example, one or more of the optical disk 19, the magnetic disk 18, the ROM 21, and the RAM 22 can be used as the storing unit.

The image generated by the image generation unit 30 is preferably a three-dimensional image.

<<Details of Operation of Control Unit 31 and Image Generation Unit 30>>

Figure 3:
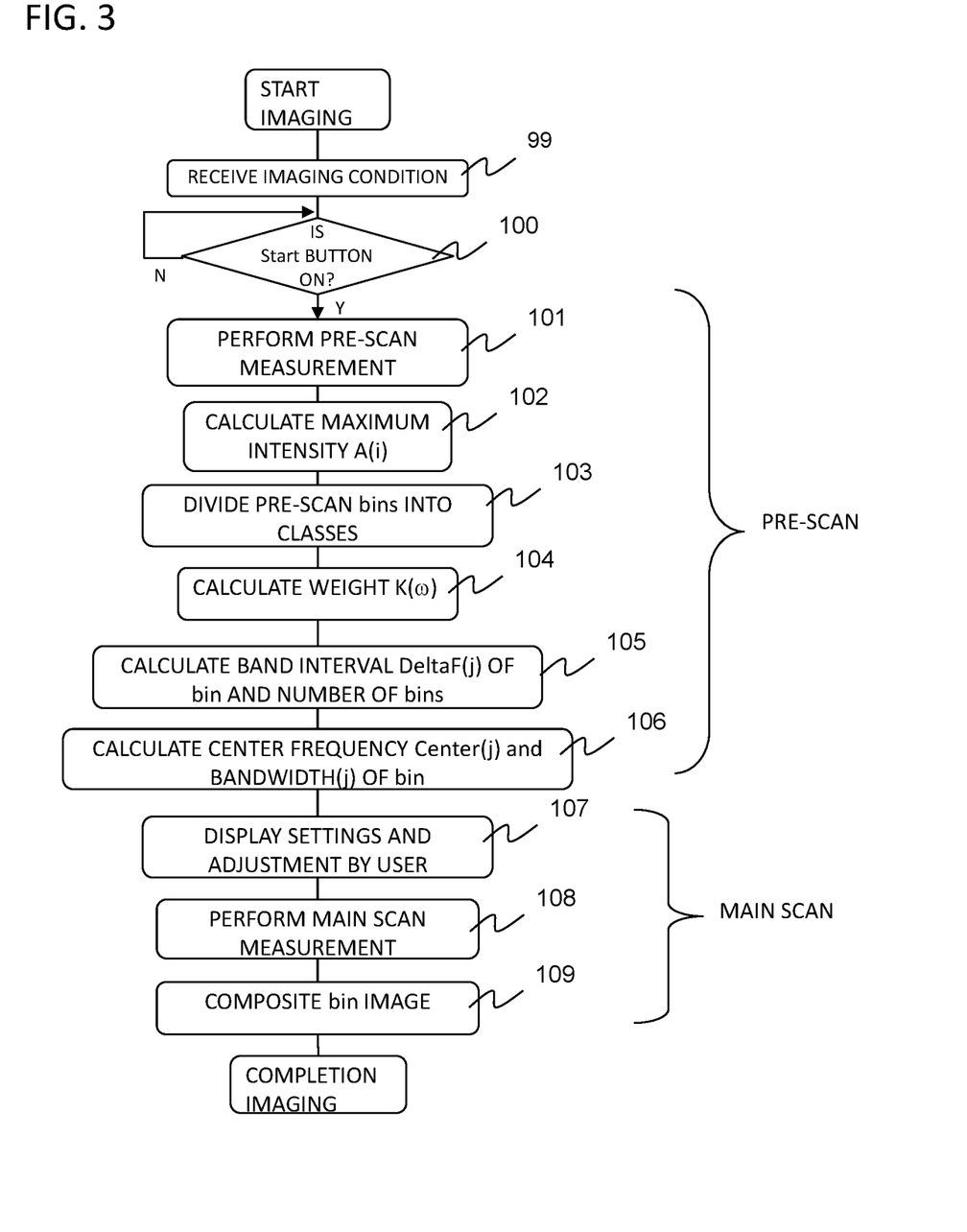
FIG. 3 is a flowchart illustrating the operation of a control unit and an image generation unit in the embodiment.

A detailed example of the operations of the control unit 31 and the image generation unit 30 will be described below with reference to the flowchart of FIG. 3.

Figure 4:
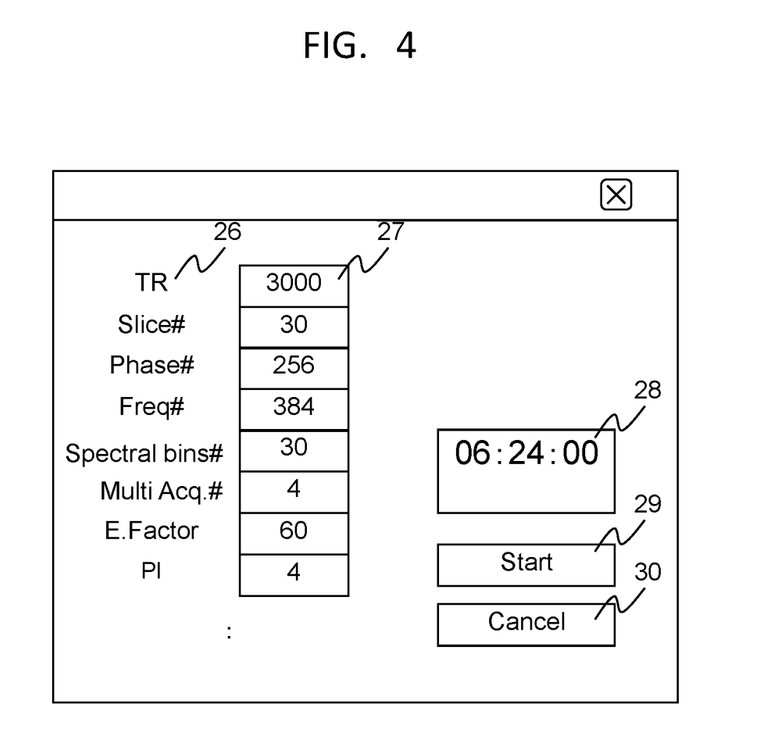
FIG. 4 is an example of an imaging condition input screen displayed on a display in the embodiment.

The control unit 31 displays an input screen of an imaging condition as illustrated in FIG. 4 on the display 20 and receives an input of the imaging condition through the operation unit 25 (step 100). The control unit 31 displays the names of a plurality of parameters of the imaging conditions for receiving the input in an area 26 of the input screen in a vertically arranged manner and receives an input of a parameter value from the operator in an input column 27 on the right side. On the input screen, an area 28 for displaying the imaging time calculated by the control unit 31 using each parameter and buttons 29 and 30 for receiving start and stop of imaging from the operator are also displayed. Among the parameters displayed in the area 26, "TR" is the repetition time, "Slice #" is the number of slice encode gradient magnetic fields to be set in a main scan, "Phase #" is the number of phase encode gradient magnetic fields to be set in the main scan, "Freq #" is the score of the frequency encode gradient magnetic field to be set in the main scan, "Spectral bins #" is the number of bins (frequency bands) to be set by the pre-scan, "MultiAcq. #" is the number of times when the number of bins set by "Spectral bins #" is image-captured a plurality of times, "E.Factor" is the number of echo trains when the pre-scan and main scan are photographed by an FSE sequence, and "PI" is a high speed multiple (thinning rate) of parallel measurement.

The control unit 31 calculates the imaging time "ScanTime" required for the main scan from the following expression (1) using the value of each inputted parameter and displays the imaging time in the area 28 of the input screen. However, in step 105 to be described later, since the control unit 31 reduces the number of bins in the main scan than the value set in "Spectral bins #", the imaging time calculated here is the imaging time when capturing an image without reducing the number of bins.

$$\text{ScanTime} = TR \times \text{Slice\#} \times \text{Phase\#} \times \text{MultiAcq.\#}/(E.\text{Factor} \times PI) \quad (1)$$

As illustrated in an expression (2), "TR" becomes longer as the value of "MultiAcq. #" (the number of divisions of bin) is small and the number of bins executed with one "TR" increases. Also, it is generally known that the larger "Spectral bins #" (the larger the total number of bins to be captured) is, the greater the effect of reducing metal artifacts is. However, in the present embodiment, metal artifacts are reduced while reducing the number of bins to be captured in steps 105 and 106.

$$TR \propto \text{Spectral bins\#} \text{MultiAcq.\#} \quad (2)$$

Figure 5:
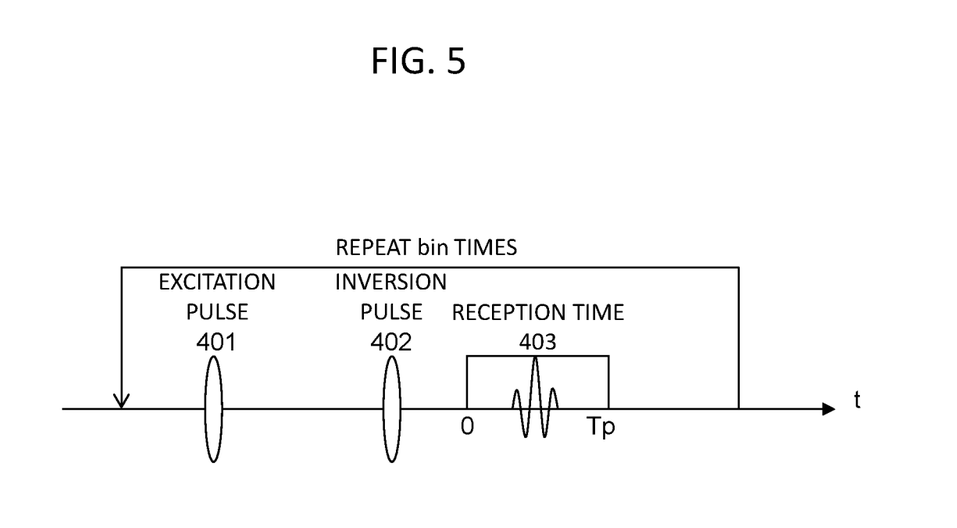
FIG. 5 is an explanatory diagram illustrating a pre-scan pulse sequence in the embodiment.

Next, when the button 29 is pressed by the operator, the control unit 31 performs pre-scan measurement of the pulse sequence of FIG. 5 (step 101).

Figure 6A:
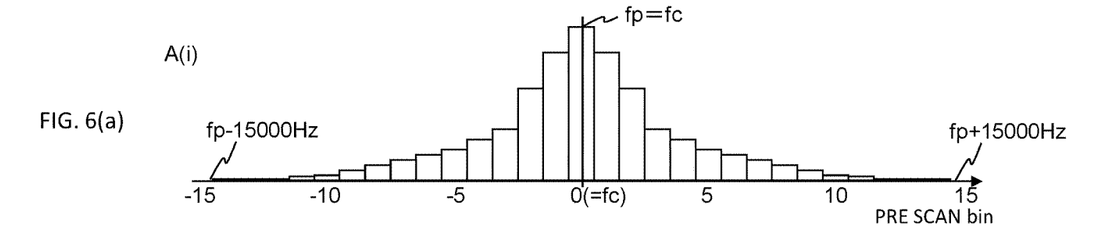

First, the control unit 31 sets the number of bins for pre-scan to the number (31 in this case) which is obtained by adding 1 to the value set in "Spectral bins #" as illustrated in FIG. 6(a). Specifically, a total of 31 bins are set by setting frequency bands (bin) by the number (15 bins) obtained by multiplying the value of "Spectral bins #" multiplied by ½ in the positive and negative directions, respectively, while shifting from the predetermined center frequency fc by a predetermined frequency bandwidth (here, 1000 Hz). With this configuration, the frequency bands (bins) from the center frequency fcp −15000 Hz to fc +15000 Hz are set. These bins are called pre-scan bins. In this case, for the bin number, the bin number is 0 for the bin including the center frequency fc, positive numbers are assigned to the bins whose frequencies are shifted from the center frequency fp in the positive direction in order from the one closest to the center frequency fp and negative numbers are assigned to the bins whose frequencies are shifted in the negative direction in order from the one closest to the center frequency fp. In the static magnetic field generated in the space where the subject 1 is disposed by the static magnetic field generation system 2, the center frequency fc may be set to a frequency at which the target spin (atomic nucleus: proton, for example) of the subject 1 is excited.

Then, the control unit 31 activates the sequencer 4 to sequentially irradiate the excitation high frequency pulse (90° pulse) 401 and the inversion high frequency pulse (180° pulse) 402 from the high frequency coil 14a as in the pulse sequence of FIG. 5, and detects the NMR signal received by the high frequency coil 14b at the reception time 403. This pulse sequence is repeated by the number of pre-scan bins by setting the irradiation frequency band of the high frequency pulses 401 and 402 and the detection frequency band of the quadrature phase detector 16 to the pre-scan bin (frequency band). In pre-scan measurement, however, the slice selection gradient magnetic field, slice encode gradient magnetic field, phase encode gradient magnetic field, frequency encode gradient magnetic field are not applied. The NMR signal detected for each bin is denoted by S(i, t), where i indicates the number of bin and t indicates time. The time range of the reception time 403 is 0<t<Tp. The reception system 6 transmits all the NMR signals S(i, t) obtained for each bin to the signal processing system 7.

In step 102, the control unit 31 obtains the maximum intensity A(i) for each bin in the t direction, from the received NMR signal S (i, t). However, i indicates the number of bin. Distribution of maximum intensity A(i) for each bin is illustrated in FIG. 6(a). The NMR signal is the largest in the bin including a certain frequency fp (here, fp=fc), and broadly widens in the frequency direction. Widening of the NMR signal distribution broadly in the frequency direction indicates that the excitation frequency of the spin is shifted due to the magnetic field generated by the metal embedded in the subject 1. The disturbance of the static magnetic field due to the magnetic field generated by the metal becomes larger as the distance from the metal becomes closer and becomes smaller as the distance from the metal becomes farther. In the MRI device with the static magnetic field intensity of 1.5 T, the frequency difference of the excitation frequency with respect to the frequency fp is about 10000 Hz due to the spin of the subject 1 positioned closest to the metal. FIG. 6(a), an NMR signal detected by a bin having a frequency difference of −2000 Hz to 2000 Hz with respect to the frequency fp is a signal from a subject spin which is hardly disturbed by a magnetic field away from a metal, and has stronger signal intensity than the other bins when an occupation ratio of the metal to the imaging site is small. On the contrary, the NMR signal detected at the bin whose frequency difference with respect to the frequency fp is close to −10000 Hz or 10000 Hz is a signal from a spin positioned in a narrow region in the vicinity of the metal, and has weaker signal intensity than the other bins.

Next, the control unit 31 sets the bin used in the main scan measurement by executing the following steps 103 to 107. By this processing, the number of bins is reduced as compared with that during pre-scan, and as illustrated in FIG. 2, adjacent frequency bands among the frequency bands 220-(−N/2) to 220-(+N/2) are set so as to partially overlap each other. In addition, the control unit 31 sets each of the frequency bands 220-(−N/2) to 220-(+N/2) so that the bandwidth of the frequency band 220-0 including the specific frequency f0 is the narrowest and the bandwidth widens stepwise or continuously in a direction away from the specific frequency f0.

Figure 6B:
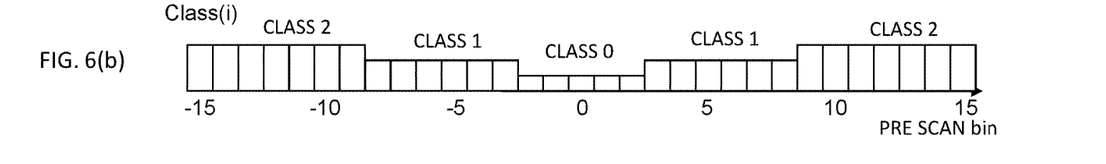
FIG. 6(b) is a graph illustrating the result of dividing the bins of the pre-scan of FIG. 6(a) into classes.

First, in step 103, the control unit 31 divides the bins of the pre-scan into classes with the bin containing the frequency fp (=fc) at which the maximum intensity A(i) was obtained as the center by the following expression (3) as illustrated in FIG. 6(b). Here, since fifteen bins are set in each of the positive and negative directions with the bin including the frequency fp (=fc) as the center, the bin number i is $-15<i<15$. According to the first expression of the expression (3), a total of 5 bins of a bin of i=0 including the center frequency fp and two positive and two negative bins around the bin are classified as class 0. By using the second expression, 10% of the maximum intensity A(0) of bin with i=0 is set as a threshold and the bin with the maximum intensity A (i) larger than the threshold is set as class 1. The remaining bins are set as class 2. However, Class(i) indicates a class of a bin number i.

if $-3<i<3$ then Class($i$)=0 else if $A(0) \times 0.1 < A(i)$ then Class($i$)=1 else then Class($i$)=2     (3)

Figure 6C:
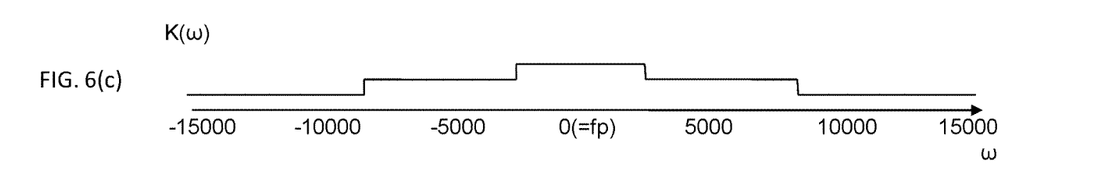
FIG. 6(c) is a graph illustrating weights K(ω) set in the bins of the pre-scan of FIG. 6(b)

Next, in step 104, the control unit 31 sets the weight $K(\omega)$ for each class set in step 103 according to the expression (4). Here, ω is a frequency difference from the frequency fp, and its range is from −15000 Hz to 15000 Hz. With this configuration, as illustrated in FIG. 6(c), the weight $K(\omega)$ =1.5 is set in the frequency range of the class 0 bin, the weight $K(\omega)$=1 is set in the frequency range of the class 1 bin, and the weight $K(\omega)$=0.5 is set in the frequency range of the class 2 bin.

if Class($i$)=$N$ then $K(\omega)=(3-N)/2$     (4)

where, $-(i+1)/2 \times 1000$ Hz$<\omega<(i+1)/2 \times 1000$ Hz

Figure 6D:
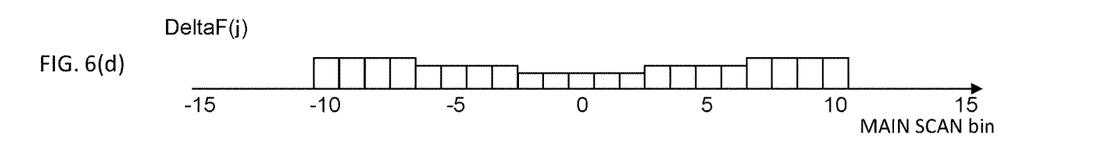
FIG. 6(d) is a graph illustrating obtained results of the bins and DeltaF(j) of a main scan using the weights in FIG. 6(c)

Next, in step 104, the control unit 31 uses the weight $K(\omega)$ set in step 104 to calculate the interval (the center frequency difference of adjacent bins) DeltaF(j) of the frequency bands of the bins of main scan as illustrated in FIG. 6(d) according to the following expressions (5) to (7). However, the frequency fp at which the NMR signal of the maximum intensity is obtained in the pre-scan is set as the specific frequency f0 (=fp) of the bin of main scan. The bin number of the main scan is set as j, the total number of the bins of the main scan is set as SumJ, and the sum of $K(\omega)$ for each bin number is set as SumK(j). The frequency fp of the pre-scan is set as a specific frequency f0 of the bin of the main scan. For the bin number j of the main scan, j=0 is set for the bin including the specific frequency f0 (=fp), for bins whose frequencies are shifted from the specific frequency f0 in the positive direction, positive numbers are assigned in order from the one closest to the center frequency f0, and for the bins whose frequencies are shifted in the negative direction, negative numbers are assigned in order from the one closest to the specific frequency f0. As illustrated in expressions (5) to (7), the bandwidth of each bin of the main scan is obtained by repetitive arithmetic operation using ω. Also, for ( ) indicates repetitive arithmetic operation, += indicates addition to itself, and −= indicates subtraction to itself.

First, by the first expression of the expression (5), the interval (here, 1000 Hz) of a predetermined frequency band is set to the bin number j=0 of the main scan. Next, by the second expression of the expression (5), it indicates that the bin number j=0 is included in the total number SumJ of bins of the main scan.

Delta$F$(0)=1000

Sum$J$=1     (5)

Next, SumK(j) and DeltaF(j) at the bin number j=1 of the main scan are initialized to 0 by the first expression of the expression (6). Next, by the second expression of the expression (6), the repetitive arithmetic operation of co in the positive direction from the initial value (here, since the center frequency difference DeltaF(0) between the bin number j=0 and the adjacent bin is 1000 Hz, 500 Hz divided by positive and negative) to the maximum frequency (here, 15000 Hz) is started. Next, by the third expression of the expression (6), the weight $K(\omega)$ is added to SumK(j) from the bin number j=1 of the main scan until SumK(ω) reaches the predetermined weight (1000 in this case) and adds the number of times of repetitions of co to the DeltaF(j). Next, by the fourth expression of the expression (6), when the SumK(ω) reaches the predetermined weight (1000 in this case), the bin number j is incremented to the next j, and the SumK(j) and DeltaF(j) at the bin number are initialized to 0. When the repetitive arithmetic operation is ended, the center frequency difference DeltaF (j) between adjacent bins for the bin number j of positive number is obtained and the maximum value of bin number j is obtained.

$j$=1,Sum$K(j)$=0,Delta$F(j)$=0 for (ω=500,ω≤15000,ω+=1)

if Sum$K(j)$<1000 then Sum$K(j)$+=$K(\omega)$,Delta$F(j)$+=1, else then $j$+=1,Sum$K(j)$=0,Delta$F(j)$=0     (6)

Next, the maximum value j of the bin number is added to the total number SumJ of the bin by the expression (7).

Sum$J$+=$j$     (7)

Next, the center frequency difference DeltaF(j) between adjacent bins for the negative number bin number j is obtained and the minimum value of the bin number j is obtained, by the expression (8) obtained by repeatedly computing co in the negative direction in the same way as in the expression (6).

$j$=−1,Sum$K(-1)$=0,Delta$F(-1)$=0 for (ω=−500,ω≥−15000,ω−−)

if Sum$K(j)$<1000 then Sum$K(j)$+=$K(\omega)$,Delta$F(j)$+=1, else then $j$−=1;Sum$K(j)$=0,Delta$F(j)$=0     (8)

Next, the minimum value j (in this case, negative) of the bin number is subtracted from the total number SumJ by the expression (9). With this configuration, the total number of bins SumJ in the main scan is obtained.

Sum$J$−=$j$     (9)

According to the step 106 described above, the number of bins in the main scan is reduced to be smaller than the number of bins of the pre-scan.

Figure 6E:
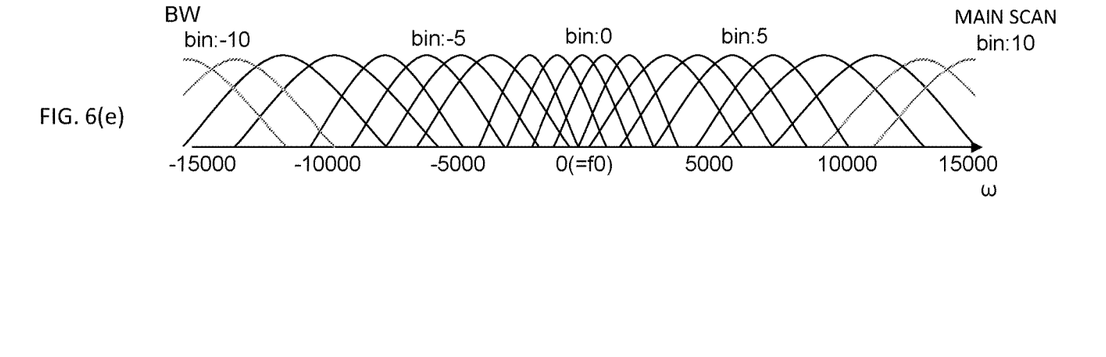
FIG. 6(e) is a graph illustrating the frequency bands of the bins of the main scan set using DeltaF(j) in FIG. 6(d).

Next, in step 106, the control unit 31 obtains the frequency bandwidth BW(j) of the bin of the main scan and the center frequency Center(j) of the frequency band from the interval DeltaF(j) of the frequency band of each bin set in step 105 by the expressions (10) and (11). However, the center frequency Center(j) is indicated by a difference from the specific frequency f0. First, as illustrated in the first expression of the expression (10), the bandwidth of the bin of the bin number j=0 of the main scan is set to 2250 Hz. For the bins other than the bin with the bin number j=0, the bandwidth is set by the second expression of the expression (10). The center frequency of the bin with bin number j=0 of the main scan is set to 0 (that is, f0) as in the first expression of expression (11). For the bins that have the positive bin number at the bin umber other than the bin number j=0, the bandwidth is set by the second expression of the expression (11), and for the other bins, the bandwidth is set by the third expression of the expression (11).

$$BW(0)=2250\ Hz$$

$$BW(j)=BW(0)/(\text{Delta}F(0)/\text{Delta}F(j)) \quad (10)$$

$$Center(0)=0$$

$$\text{if } j>0 \text{ then } Center(j)=Center(j-1)+\text{Delta}F(j) \quad (11)$$

$$\text{else then } Center(j)=Center(j-1)-\text{Delta}F(j)$$

Figure 7:
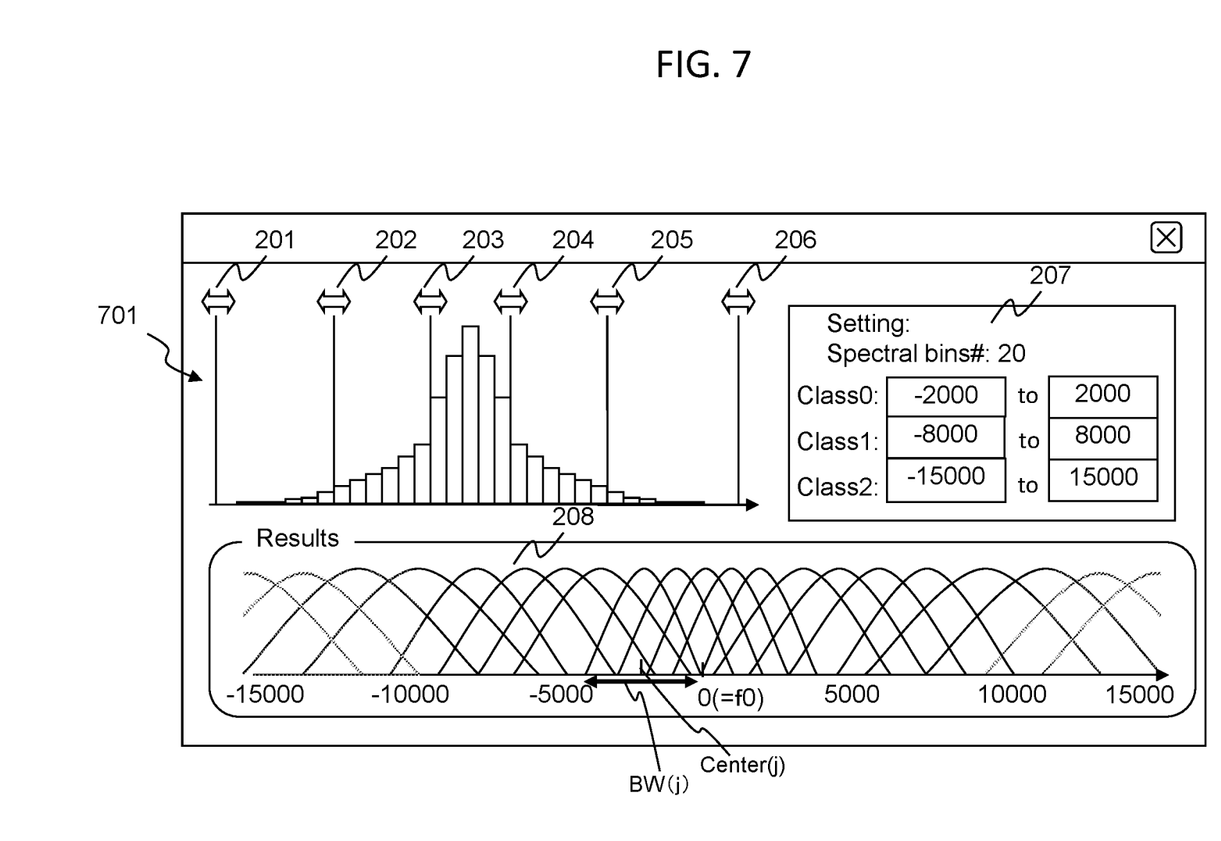
FIG. 7 illustrates a result of the pre-scan in the embodiment and the frequency bands of a set main scan, and is an example of a screen for receiving adjustment by the user.

The control unit 31 displays the maximum intensity A(i) of the NMR signal of each bin obtained in step 102 and Class (i), BW (j), and Center (j) obtained in steps 103 to 106 on the display 20 and receives the setting of bin by the user. In FIG. 7, a screen displayed on the display 20 is illustrated. In an area 701 of the screen of FIG. 7, the maximum intensity A(i) of the NMR signal of each bin is displayed, and the line segment 201 indicates a lower limit value of class 2, which can be changed by the user operating the operation unit 25. Similarly, a line segment 202 indicates a lower limit value of class 1, a line segment 203 indicates the lower limit value of class 0, a line segment 204 indicates the upper limit value of class 0, a line segment 205 indicates the upper limit value of class 1, a line segment 206 indicates the upper limit value of class 2, all of which can be changed by the user. In an area 207 of the screen, the upper limit value, the lower limit value, and the total number of bins of each class are displayed as numerical values. The user can change the upper limit value and the lower limit value of each class by changing the numerical values of the upper and lower limit values. Further, in an area 208 of the screen, the frequency bandwidth BW(j) of each bin and the center Center(j) of the frequency band are displayed. When the user changes the upper limit value or the lower limit value of each class on the screen area 701 or 207, the control unit 32 updates BW (j) and Center (j) by calculating the steps 104 to 106 again, and illustrates the updated value in the screen area 208.

Next, the control unit 31 activates the sequencer 4 and executes a main scan for acquiring an image. In the main scan, after a high frequency pulse for excitation (90° pulse) 401 and a high frequency pulse for inversion (180° pulse) 402 are sequentially irradiated from the high frequency coil 14a like the pre-scan, a slice encode gradient magnetic field and a phase encode gradient magnetic field are applied and an NMR signal is received at a reception time 403 while applying a frequency encode gradient magnetic field unlike pre-scan. This is repeated while changing the value of the slice encode gradient magnetic field by the number of the slice encode gradient magnetic fields input to "Slice #" in step 99 and the value of the phase encode gradient magnetic field by the number of phase encode gradient magnetic fields input to Phase #", respectively. With this configuration, the number of NMR signals necessary for reconfiguration of the three-dimensional image is acquired. In the pulse sequence, the sequencer 4 does not apply the slice selection gradient magnetic field. In order to realize the frequency bandwidth BW(j) obtained in step 106, an application time Duration (j) of the RF wave is applied as short as the reciprocal of BW from Duration (0) of the center Bin as in the expression (12).

$$Duration(j)=Duration(0)\times BW(0)/BW(j) \quad (12)$$

The image generation unit 30 reconfigures a three-dimensional image using the acquired NMR signal. The control unit 32 can obtain a three-dimensional image for each bin of the main scan by repeating the pulse sequence for each bin of the main scan and by the image generation unit 30 repeating the operation of reconfiguring the three-dimensional image using the obtained NMR signal.

In step 109, the image generation unit 30 composites (for example, sum-of-square composites) the three-dimensional images obtained for each bin of the main scan, and displays the composited image on the display 20. With this configuration, it is possible to capture a three-dimensional image in which disturbance of an image due to the metal implanted in the subject 1 is suppressed while reducing the number of bins of the main scan and shortening the imaging time.

As described above, in the present embodiment, it is possible to shorten the imaging time while obtaining the effect of reducing the disturbance of the image due to the distortion of the magnetic field by the metal implanted in the subject 1.

In the embodiment described above, a configuration in which the number of classes and weights used for classification of pre-scan bin may be adjusted by the user may be adopted. With this configuration, the user can more flexibly select the distortion reduction effect and the imaging time.

In order to realize a wider frequency bandwidth BW(j) than in the related art, a composite pulse or adiabatic passing pulse may be used as the high-frequency magnetic field pulse.

Further, in the embodiment described above, the number of times of repetitions SumJ (the total number of bins) of the main scan differs depending on the result of the pre-scan. For that reason, it is impossible to predict a specific absorption rate (SAR) including the main scan before imaging of the pre-scan, but the imaging is divided into the pre-scan measurement and the main scan measurement, and only the pre-scan measurement may be executed in advance, and the SAR of the main scan may be predicted and displayed according to the result of the pre-scan measurement.

Further, the frequency bandwidth BW(j) and the like of each bin may be displayed on the display 20.

In the present embodiment, the upper limit value and the lower limit value of the class are determined by the pre-scan, but input of the lower limit value and the upper limit value of the class from the user may be received in the imaging condition input screen without performing the pre-scan.

Although one embodiment of the present invention has been described above, the present invention is not limited to the embodiment described above, and can be appropriately changed.

REFERENCE SIGNS LIST

1: subject
2: static magnetic field generation system
3: gradient magnetic field generation system
4: sequencer
5: transmission system
6: reception system
7: signal processing system
8: central processing unit (CPU)
9: gradient magnetic field coil
10: gradient magnetic field power supply
11: high frequency oscillator
12: modulator
13: high frequency amplifier
14a: high-frequency coil (transmission coil)
14b: high-frequency coil (receiving coil)
15: signal amplifier 16: quadrature phase detector
17: A/D converter
18: magnetic disk
19: optical disk
20: display
21: ROM
22: RAM
23: track ball or mouse
24: keyboard
30: image generation unit
31: control unit
220: frequency band
230: high-frequency magnetic field pulse

The invention claimed is:

1. A magnetic resonance imaging device comprising:
a static magnetic field generation unit that generates a uniform static magnetic field in a space for accommodating a subject;
a transmission unit that irradiates a high-frequency magnetic field pulse for exciting the subject;
a reception unit that receives an NMR signal generated by the subject irradiated with the high-frequency magnetic field pulse;
an image generation unit that generates an image from the NMR signal; and
a control unit,
wherein the control unit sets a plurality of frequency bands within a predetermined frequency range, causes the subject to be irradiated with the high-frequency magnetic field pulse having one of the plurality of frequency bands from the transmission unit, causes the reception unit to receive the NMR signal generated by the subject, causes the image generation unit to repeatedly perform an operation for generating the image from the NMR signal while changing the frequency bands, obtains a plurality of images respectively corresponding to the plurality of frequency bands, and composites the plurality of images, and
the control unit sets the plurality of frequency bands so that adjacent frequency bands partially overlap each other, and a bandwidth of the plurality of frequency bands is narrowest for the frequency band including a specific frequency within the frequency range and stepwise or continuously widens in a direction away from the specific frequency.

2. The magnetic resonance imaging device according to claim 1,
wherein the specific frequency is a frequency at which the NMR signal generated by the subject has a highest intensity when irradiating the subject with high-frequency magnetic field pulses of a plurality of frequencies constituting the predetermined frequency range.

3. The magnetic resonance imaging device according to claim 1,
wherein the control unit executes a pre-scan in which the subject is caused to be irradiated with the high-frequency magnetic field pulse of a plurality of preset frequencies constituting the predetermined frequency range from the transmission unit and the reception unit is caused to receive the NMR signal generated by the subject for each of the plurality of frequencies, thereby obtaining the specific frequency.

4. The magnetic resonance imaging device according to claim 3,
wherein the control unit sets the bandwidth of the frequency band corresponding to an intensity of the NMR signal obtained by the pre-scan.

5. The magnetic resonance imaging device according to claim 1,
wherein the high-frequency magnetic field pulse has intensity distribution within the frequency band, and a profile obtained by summing intensities of the plurality of high-frequency magnetic field pulses for each frequency is continuous in a frequency direction.

6. The magnetic resonance imaging device according to claim 1,
wherein the control unit selects one type from among a plurality of types of frequency band patterns which are prepared in advance and in which at least one of a bandwidth of the plurality of frequency bands and a degree of overlapping of adjacent frequency bands is different, thereby setting the plurality of frequency bands.

7. The magnetic resonance imaging device according to claim 6, further comprising:
an operation unit that receives information of a metal embedded in the subject from an operator,
wherein the control unit selects one type from among the plurality of types of frequency band patterns according to the information of the metal received from the operator by the operation unit.

8. The magnetic resonance imaging device according to claim 1, further comprising:
a storing unit that stores patterns of a plurality of types of the frequency bands which are obtained in advance,
wherein the control unit executes a pre-scan in which the subject is caused to be irradiated with the high-frequency magnetic field pulse of a plurality of preset frequencies constituting the predetermined frequency range in order, from the transmission unit and the reception unit is caused to receive the NMR signal generated by the subject for each of the plurality of frequencies and sets the plurality of frequency bands by selecting the pattern of the frequency bands stored in the storing unit based on intensity distribution of the received NMR signal.

9. The magnetic resonance imaging device according to claim 1,
wherein the image is a three-dimensional image.

10. An imaging method using a magnetic resonance imaging device including a static magnetic field generation unit that generates a uniform static magnetic field in a space for accommodating a subject, a transmission unit that irradiates a high-frequency magnetic field pulse for exciting the subject, a reception unit that receives an NMR signal generated by the subject irradiated with the high-frequency magnetic field pulse, an image generation unit that generates an image from the NMR signal, and a control unit, the method comprising:
by the control unit, causing the subject to be irradiated with the high-frequency magnetic field pulse having one of a plurality of frequency bands which are set within a predetermined frequency range from a transmission unit; causing the reception unit to receive the NMR signal generated by the subject; causing the image generation unit to repeatedly perform an operation for generating the image from the NMR signal while changing the frequency band; obtaining a plurality of images respectively corresponding to the plurality of frequency bands; and compositing the plurality of images, wherein adjacent frequency bands partially overlap each other in the plurality of frequency bands, and a bandwidth of the plurality of frequency bands is narrowest for the frequency band including a specific frequency within the frequency range, and stepwisely or continuously widens in a direction away from the specific frequency.

* * * * *